(12) United States Patent
Burgett et al.

(10) Patent No.: US 9,258,678 B2
(45) Date of Patent: Feb. 9, 2016

(54) CLOSED LOOP ATHLETE TRAINING SYSTEM

(71) Applicant: Harman International Industries, Incorporated, Stamford, CT (US)

(72) Inventors: Seth D. Burgett, Glen Carbon, IL (US); Effrosini A. Karayiannis, St. Louis, MO (US); Richard J. Daniels, St. Louis, MO (US); Michael Joseph Spenner, Town & Country, MO (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

(21) Appl. No.: 14/216,762

(22) Filed: Mar. 17, 2014

(65) Prior Publication Data

US 2014/0273925 A1    Sep. 18, 2014

Related U.S. Application Data

(60) Provisional application No. 61/794,232, filed on Mar. 15, 2013.

(51) Int. Cl.
*H04M 11/00* (2006.01)
*H04W 4/02* (2009.01)
(Continued)

(52) U.S. Cl.
CPC ............ *H04W 4/027* (2013.01); *A61B 5/681* (2013.01); *A61B 5/6803* (2013.01); *G06F 19/3481* (2013.01); *G09B 19/0038* (2013.01); *H04M 1/72558* (2013.01); *H04M 1/72572* (2013.01); *H04M 15/58* (2013.01); *A61B 5/0024* (2013.01); *A61B 5/02055* (2013.01); *A61B 5/02438* (2013.01); *A61B 5/1118* (2013.01); *A61B 5/14517* (2013.01); *A61B 5/14532* (2013.01);
(Continued)

(58) Field of Classification Search
CPC ...... H04W 4/26; H04W 4/027; A61B 5/0002; A61B 5/16; A61B 5/6803; A61B 5/681; A61B 5/0024; A61B 5/02055; A61B 5/02438; A61B 5/1118; A61B 5/14517; G06F 19/3481; G09B 19/0038; H04M 1/72558; H04M 1/72572; H04M 15/58
USPC ............... 455/405; 434/247; 482/9; 600/301; 700/91
See application file for complete search history.

(56) References Cited

U.S. PATENT DOCUMENTS 8,781,568 B2 * 7/2014 Dugan et al. .................. 600/519
2010/0273610 A1 10/2010 Johnson
(Continued)

FOREIGN PATENT DOCUMENTS

WO    WO-2008030484 A2    3/2008
WO    WO 2008030484 A3 *  7/2008

OTHER PUBLICATIONS

International Search Report and Written Opinion for PCT/US2014/030637 Dated: Oct. 14, 2014 pp. 13.

*Primary Examiner* — Amancio Gonzalez
(74) *Attorney, Agent, or Firm* — Brooks Kushman P.C.

(57) ABSTRACT

An athletic training system includes a personal electronic device having a processor, a memory, and a GPS sensor. The processor runs an application that calculates at least one of distance traveled, elevation change, and speed, of the user carrying the personal electronic device, and based upon location information obtained from the GPS sensor provides a training-related message to the user based upon at least one of the calculated distance traveled, elevation change, and speed.

13 Claims, 1 Drawing Sheet

(51) Int. Cl.
  *H04M 15/00* (2006.01)
  *H04M 1/725* (2006.01)
  *G06F 19/00* (2011.01)
  *G09B 19/00* (2006.01)
  *H04L 29/08* (2006.01)
  *A61B 5/00* (2006.01)
  *A61B 5/0205* (2006.01)
  *A61B 5/024* (2006.01)
  *A61B 5/11* (2006.01)
  *A61B 5/145* (2006.01)

(52) U.S. Cl.
  CPC ........... *A61B 5/14542* (2013.01); *A61B 5/4875* (2013.01); *A61B 5/7495* (2013.01); *A61B 2503/10* (2013.01); *H04L 67/12* (2013.01); *H04M 2250/12* (2013.01)

(56) References Cited

U.S. PATENT DOCUMENTS

| | | | |
|---|---|---|---|
| 2012/0078396 A1* | 3/2012 | Case et al. | 700/91 |
| 2012/0116550 A1 | 5/2012 | Hoffman et al. | |
| 2012/0226112 A1* | 9/2012 | LeBoeuf et al. | 600/301 |
| 2014/0188658 A1* | 7/2014 | Li et al. | 705/26.8 |
| 2014/0343861 A1* | 11/2014 | Edman et al. | 702/19 |

* cited by examiner

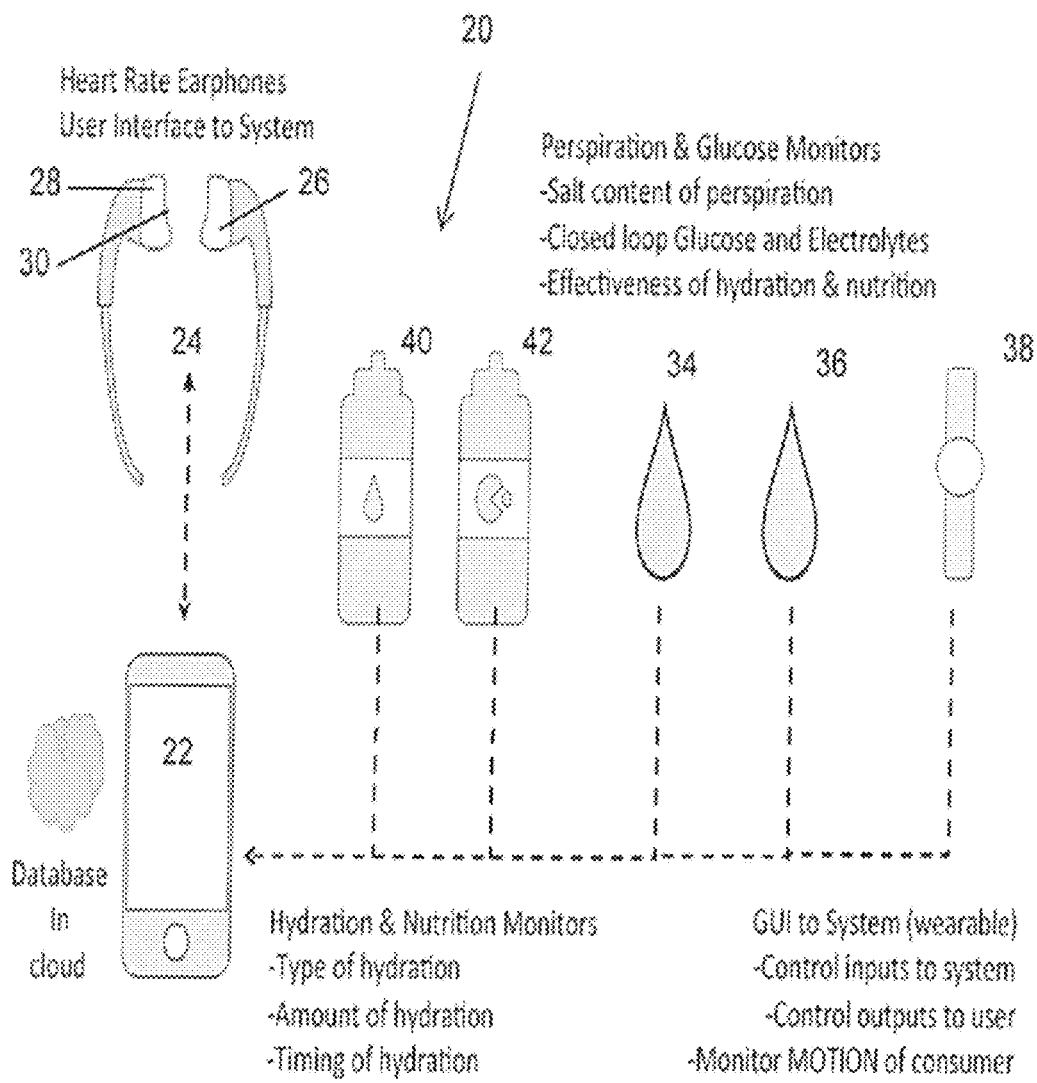

CLOSED LOOP ATHLETE TRAINING SYSTEM

CROSS-REFERENCE TO RELATED APPLICATIONS

This application claims priority to U.S. Provisional Patent Application Ser. No. 61/794,232, filed Mar. 15, 2013. The entire disclosure of the above-referenced application is incorporated herein.

FIELD

The present disclosure relates to an athlete training system, and in particular, to an automated system for directing athletic training.

BACKGROUND

This section provides background information related to the present disclosure which is not necessarily prior art.

There is an increasing emphasis on living healthy lifestyles and a large segment of the population is participating in activities that support such lifestyles. This includes a growing trend of participation in endurance sports. Healthy lifestyles, the training behind endurance sports, and athletic lifestyles all center on proper nutrition, hydration and an appropriate exercise regimen. However, misinformation abounds, but even well informed individuals have difficulty achieving optimal training.

SUMMARY

This section provides a general summary of the disclosure, and is not a comprehensive disclosure of its full scope or all of its features.

Embodiments of the present invention provide systems and methods for improving an individual's athletic training. Utilizing "smart" phones which provide a computer processor and wireless communication, together with information input by the user or obtained from one or more of a variety of sensors, systems and methods are provided to optimize one or more aspects of athletic training, including for example, scheduling, nutrition, and fluid intake.

Examples of sensors that can be used include condition sensors, such as location, elevation and temperature sensors; intake and consumption sensors, such as fluid intake and calorie consumption sensors; performance sensor, such as distance, speed, and acceleration sensors; and health sensors, such as body temperature, pulse rate, blood pressure, and sweat sensors.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a schematic diagram of a preferred embodiment of a system in accordance with the principles of this invention.

Corresponding reference numerals indicate corresponding parts throughout the several views of the drawings.

DETAILED DESCRIPTION

Example embodiments will now be described more fully with reference to the accompanying drawings.

A preferred embodiment of an athletic training system in accordance with the principles of this invention is indicated generally as 20 in FIG. 1. The system 20 can comprise a personal electronic device (PED) 22, such as an iPhone or any other "smart" phone with a processor, memory, and wireless communication capabilities. The PED preferably also has a keypad or a touch screen to allow for input and output from one or more apps running on the processor of the PED. The PED 22 preferably has both distance (e.g., cellular or wi-fi) communication capability, as well as local (e.g., Bluetooth) communication capability. The PED 22 preferably also includes music storage and playback capabilities, such as an MP3 player.

The PED 22 preferably also includes an integral GPS sensor for determining the current location of the PED, and thus the user, as well as determining changes in current location (i.e., distance traveled and elevation change), and the rate of change (i.e. speed). This information can be used by an application running on the PED 22 to guide the user's training.

The PED 22 preferably also includes an accelerometer which measures the acceleration of the PED, and thus of the user. This information can be used by an application running on the PED 22 to guide the user's training.

The system preferably also comprises earphones or headphones 24. The earphones 24 can have a wired or wireless (e.g. Bluetooth) connection to the PED 22, and allow the user to listen to music being played by the PED 22. In some embodiments the system can control the selection of songs and/or the speed of playback as a method of controlling the user's training. In addition to playing music, the earphones 24 also provide a way for the system to give aural feedback to the user, for example, an application running on the PED 22 could generate verbal instructions or words of encouragement for the user, which could be transmitted to the user via the earphones 24.

A heart rate or pulse sensor 26 can be incorporated into the earphones 24 to provide heart rate or pulse data via the wired connection, or preferably wireless to the PED 22. A temperature sensor 28 and/or a blood oxygenation sensor 30 could also be incorporated into the earphones 24 to provide temperature data and blood oxygenation data via the wired connection, or preferably wireless to the PED 22. This information can be used by an app running on the PED 22 to guide the user's training.

A separate motion sensor can be provided in addition to, or instead of the motion sensor included in the PED 22. This motion sensor can be an accelerometer, or a microwave, infrared, ultrasonic, or tomographic sensor. The sensor may be incorporated into either a wrist worn device, such as a sport watch, or into a foot worn device, such as a device that attaches to the user's shoes or is embedded in the user's shoes. In this case, the device could measure either the arm movement or the leg movement of the user, to provide further information about the user's exertion to the PED. This information is preferably communicated wireless to the PED 22, such as via Bluetooth.

The system can include sensors 34 and 36 for measuring glucose and electrolytes, for example from the user's sweat. This information can be used by an app running on the PED 22 to guide the user's workout, including directing the user to increase or decrease fluid and/or nutrition intake.

The system preferably also includes a wrist word device, such as a smart watch. 38. In addition to its function of display time and date, the smart watch can include one or more sensors to gather information for use by the system. These sensors can include GPS sensors for determining current location; a heart rate or pulse sensor (in addition to or instead of sensor 26); a body temperature sensor (instead of or in addition to temperature sensor 28); a blood oxygenation sensor (instead of or in addition to blood oxygenation sensor 30); glucose and/or electrolyte sensors for measuring the glucose, sodium, and/or other electrolytes via the user's sweat; motion sensors, as described above; an ambient temperature sensor for measuring the current weather conditions; an altitude (or pressure sensor) for measuring current elevation. In addition to these sensors, the smart watch 38 provides a convenient input and output device for the application running on the PED 22, and could even take the place of the PED. The smart watch 38 can have one or more input controls, or even a touchscreen control. The smart watch can also have a display for text or graphics to communicate information and instructions to the user.

The system preferably also can include a fluid intake sensor 40, which can be incorporated in a fluid bottle, or into a replaceable spout for a fluid bottle. The sensor can measure at least the quantity of fluid dispensed from the bottle (and presumably consumed by the user), and provide this information to the app running on the PED 22 to guide the user's training. The fluid intake sensor 40 could be provided with means to detect the nature of the fluid, e.g., whether it is plain water, or it could include a control, so that the user can set the sensor for a particular type of fluid, for example, water or sports drink. Alternatively, the user can use the interface of the PED 22 or an interface on the smart watch 38 to input the particular type of fluid. In a preferred embodiment where the PED 22 includes a camera, the user could use the camera so that the PED "reads" the bar code on the container. In other embodiments, the user can be presented with a menu on the PED 22 or the smart watch 38 and makes an appropriate selection. Special containers of fluid can be provided as part of the system that has an informational bar code or other indicia to facilitate inputting information about the fluid being consumed.

The system preferably also can include a nutritional intake sensor 42, which can be incorporated in a food package, although the information is preferably simply input by the user. The type of nutrition and the calories consumed can be provided to the app running on the PED 22 to guide the user's training. The user can use the interface of the PED 22 or an interface on the smart watch 38 to input the particular type of nutrition consumed and the quantity. In a preferred embodiment where the PED 22 includes a camera, the user could use the camera so that the PED "reads" the bar code on the package. In other embodiments, the user can be presented with a menu on the PED 22 or the smart watch 38 and makes an appropriate selection, preferably specifying both the type and quantity of nutrition consumed. Special containers of nutrition can be provided as part of the system that has an informational bar code or other indicia to facilitate inputting information about the nutrition being consumed.

The PED 22 and or the smart watch 38 provide an interface in which the user can provide personal information to the system, including gender, age, height, weight, bmi (although this could be calculated based on the other inputs), general level of fitness (although this could be determined and/or updated by the system in the course of use of the system).

Weight information could also be obtained from "smart" scales that transmit the information directly to the PED 22. The user can also input other information, including preferred training times and session durations, preferred training activities or goals (for an individual training session, or a long term goal such a marathon). This information can be used by an app running the PED to guide the workout.

The system includes one or more apps running on the PED 22 to guide the user's training based on the information input by the user and/or obtained from one or more sensors.

One app running on the PED 22 could contain or access a database of nutritional information and values. This can be a standard database or it can be a database created in whole or in part by user inputs based on the types, and quantities of foods the user actually consumes. Some embodiments of the app can run with only information about consumption during training. Other embodiments can take into account all of the user's consumption, both during and between training sessions.

Using the database and input and acquired information about the user's training and other activities, the app can determine the optimal nutrition and hydration for the user. The app can extract data from the user through inputted values, such as gender and height and from other applications, such body weight or body mass index from a "smartscale" (scale which transmits data to an application), fitness level (results from fitness benchmark tests, such as best 5k time etc., or other standardized activities), VO2, VO2 max along with heart rate information can be monitored in real time. The app will take these values and use the database to calculate the needed nutritional values and hydration values for the user. The application could then convert this into usable information for the user and suggest balanced meals and proper hydration for the user by displaying suggested food and suggested drinks. This nutrition and hydration input can be provided in the days leading up to an athletic event, such as a marathon, during the marathon and post athletic event. Each period is critical for both hydration and nutrition to properly train athletes for endurance sports in particular. Some athletes today over eat (e.g., "carb loading" prior to a marathon), and generally under hydrate during a marathon, and rarely properly hydrate or replenish with the proper carbohydrate/protein balance post event which is known to promote recovery. Recovery leads to increase athletic performance since the athlete can return to active training sooner following an athletic event like a marathon. Preferably the system can obtain information about the user's exertion, hydration, and nutrition, and use this information in an appropriate algorithm to determine and guide the user's preparation and training.

The same or a separate application can also guide the scheduling of the user's training. In one embodiment, the app can use user-inputted preferences during training, such as a preference for not training outside in inclement weather, in a specified temperature range, or in a specified time of the day. The app can use weather forecast information for the area of training (which can be determined from information from the GPS sensor), the PED 22's calendar, and the user's preferences to schedule the user's training. The user can input a training location, and the system can refer to a database to determine the machines/training devices available at the location, and suggest exercises and workout routines for the user based on goals identified by the user. During training, the user can use the interface of the PED 22 or the smart watch 38 to input the actual training activities undertaken. During training, the app can use the heart rate data obtained from the heart rate sensor to help the user achieve an optimal heart rate given their fitness goals and fitness needs. In addition, the app can use information from the glucose monitor and sweat content sensor (if available) to suggest when the user should take on fluid/food (such as gel packs, etc.), as well as indicate when not to take in food/drink.

In another embodiment, the app can measure the amount of sleep of the user and reschedule training sessions, if the proper amount of sleep has not been obtained. The application can do this in various ways, including measuring the last use of the PED 22 and if it is past a certain hour, prompt the user to reschedule the training session. For instance, if the database calculates that the user needs at least 7 hours of sleep and the last use of the phone was at 1:00 AM, and a training session is scheduled for 5:00 AM, the session should be rescheduled after 8 AM.

Thus, the system can provide one or more apps that provide a comprehensive training aid for individuals desiring a healthy lifestyle or athletes wanting to get the most out of their training. Through various sensors and user inputted data, the system is able to suggest an appropriate diet and training regimen for the user.

The system can act as a "coaching"/"logging"/"training" device for the user. The system operates on available information, which can include, but is not limited to: heart rate, VO2 Max, glucose, fluid intake, sweat content, body temperature, atmospheric pressure, atmospheric temperature, type and quantity of exercise being performed (automated or through user input). The system will be functional even if some components are missing. It will encourage the user to obtain additional accessories to provide more of the desired inputs in order to improve training guidance.

Some embodiments of the system will have the ability to suggest food and drink intake to the user, based upon database information, user input, and sensed information. The system can provide specific suggestions of food types and quantities for impending events, as well as make more long term suggestions for events in the future, as well as the timing of consumption relative to scheduled events.

The system can provide training suggestions that take into account the user's schedule and user's preferences. For example, if the user does not like to run in the rain or at temperatures below or above X, the application can use location information and weather and weather forecast data to automatically schedule training activities. The application could also suggest the best times of the day to train. If the user's calendar has two blocks of time open and one of the blocks has the preferred weather, it will schedule the workout for that time. The app can preferably work with iCalandar, Outlook, etc. to plan workouts/training with the weather and the user's schedule. Furthermore the app can preferably take into account the training partner's schedules and preferences, and determine optimum times for groups of two or more users.

The PED 22 preferably can interface with the user's alarm clock, or It can serve as the user's alarm clock, tracking the time when the user sets the alarm and the time when the user awakes to the alarm to determine sleep time, and to even manage sleep time by recommending when a user goes to bed or when a user wakes up, and dynamically adjusting alarms and alerts to achieve the training goals.

The system can have an app preset modes that allows the user to input the time and type of event (e.g. marathon, Tough Mudder, Ironman, Triathlon, etc), and the system can develop a training and/or nutrition schedule and prompt the user to follow the schedule, and automatically determine compliance with the schedule and adjust the schedule according to actual performance.

The system can also accommodate user injury, by accepting inputs of various injuries, and adjusting the schedule or the types of recommended activities accordingly.

The system can also store performance data and use the stored data to compare user performance with past user performance and with model performance. This comparison can include not just activity details, such as speed and distance of a run, but such things as resting heart rate, caloric intake, calories burned, etc. These comparisons can be used to adjust the training schedule, including types of activities and duration.

Of course the user retains the option to override any automated functions, such as rescheduling, and the system can further adjust to these overrides. The system is preferably equipped to "learn" user preference based upon conduct, including timing of training, available days for training, activity preferences, and even food and beverage preferences, and adjust future guidance suggests not just to input preferences, but learned preferences as well.

Example:

A runner is training for a marathon that is 1 month away. The runner inputs height/weight/age/sex/fitness level/BMI, etc. into the system, and an app suggests meals and times for the meals. The application automatically suggests when the meals should take place based on the time of training/exercise. The user can further input the types and quantities of food actually consumed, so that further recommendations can be adjusted and refined.

Example:

A user actually participating in a marathon can used the device to monitor hydration. The system can take inputs from a sensor enabled "smart", from a database, and from physiological sensors, such as sweat sensors and body temperature, pulse, and blood pressure sensors. The system is designed to be used with or without the smart bottle and or hydration sensor however, it will operate most efficiently with both of those elements.

The user will input which types of fluids they wish to consume or what is at their disposal. The application can also locate resources for example, locations of public fountains and stores where particular products are available. For example, if the user needs a nutritional supplement, the app can access a database where a suitable supplement is sold and use the phone's GPS to direct the user to the location of a store.

Example:

A user wakes up and is scheduled to run 8 miles for training. The app can suggest what to eat and drink and when to eat it and drink it. It can also suggest a quantity of liquid to carry, based upon the needs of the user, the available resources along the anticipated route, etc. If the user uses a sensor enabled smart bottle, the application can monitor consumption and adjust guidance accordingly.

The system can use GPS of the PED 22 to determine the speed and duration of certain trainings. If the user is biking, the GPS will record the path taken, log the speed information, and use this information to determine calories burned.

If the user has an additional sensor, such as an accelerometer in a knee brace, this sensor can be used to further refine the estimate of calories burned, etc.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An athletic training system comprising:
a personal electronic device comprising a processor, a memory, and a Global Positioning System (GPS) sensor; the processor configured to:
calculate at least one of distance traveled, elevation change, and speed based upon location information obtained from the Global Positioning System sensor,
select one or more songs stored in the memory to play to the personal electronic device, and
receive user training preferences including an ambient temperature range, receive weather information, and
provide a training-related message based on the user training preferences and weather information.

2. The athletic training system according to claim 1 wherein the processor is configured to alter to playback speed of at least one song based upon at least one of the distance traveled, elevation change, and speed.

3. The athletic training system according to claim 1 further comprising a pulse sensor in communication with the personal electronic device, and wherein the processor is configured to process a pulse rate from the pulse sensor and provide the training-related message based upon at least the pulse rate.

4. The athletic training system according to claim 1 further comprising a blood oxygenation sensor in communication with the personal electronic device, and wherein the processor is configured to process a blood oxygen level from the blood oxygenation sensor and provide the training-related message based upon at least the blood oxygenation level.

5. The athletic training system according to claim 1 further comprising a temperature sensor in communication with the personal electronic device, and wherein the processor is configured to process a user temperature from the temperature sensor and provide the training-related message based upon at least the user temperature.

6. The athletic training system according to claim 1 further comprising a sensor for measuring at least one of glucose and electrolytes in a user's sweat in communication with the personal electronic device, and wherein the processor is configured to process at least one of glucose and electrolytes from the sensor and provide the training-related message based upon at least one of the glucose and electrolytes.

7. The athletic training system according to claim 5 wherein the training-related message relates to at least one of fluid and nutrition intake.

8. The athletic training system according to claim 1 wherein the personal electronic device includes a camera, and wherein the processor is configured to process images from the camera to determine at least one of fluid and nutrition intake, and provide the training-related message based upon at least one of the fluid and nutrition intake.

9. The athletic training system according to claim 1 wherein the processor receives information about a user's vital statistics, including at least one of gender, age, height, weight, and body mass index (BMI).

10. An athletic training system comprising:
a personal electronic device comprising a processor, a memory, a camera and a Global Positioning System (GPS) sensor; the processor configured to:
receive images from the camera to determine at least one of fluid and nutrition intake,
receive user training preferences including an ambient temperature range, receive weather information, and
provide a training-related message based on at least one of the user training preferences, the weather information, and the fluid and nutrition intake.

11. The athletic training system of claim 1, wherein the processor is further configured to access a database to determine available training devices at a training location and provide the training-related message based on the available training devices.

12. The athletic training system of claim 1, wherein the processor if further configured to determine an amount of user sleep and provide the training-related message based on the amount of user sleep.

13. The athletic training system of claim 10 wherein the processor is further configured to:
receive user training preferences including an ambient temperature range,
receive weather information, and
provide the training-related message based on the training preferences and weather information.

* * * * *